United States Patent [19]

Bender

[11] Patent Number: 5,275,581
[45] Date of Patent: Jan. 4, 1994

[54] CERVICAL COLLAR

[75] Inventor: Kelly M. Bender, New Auburn, Wis.
[73] Assignee: Mikros U.S.A., Inc., Chetek, Wis.
[21] Appl. No.: 962,857
[22] Filed: Oct. 19, 1992
[51] Int. Cl.$^5$ ............................................. A61F 5/00
[52] U.S. Cl. ............................ 602/18; 128/DIG. 23; 602/5
[58] Field of Search ................ 602/5, 17-19, 602/6; 128/DIG. 23

[56] References Cited

U.S. PATENT DOCUMENTS

| | | | |
|---|---|---|---|
| 1,243,230 | 10/1917 | Smith | 602/6 |
| 2,562,121 | 7/1951 | Poux | 128/DIG. 23 X |
| 3,070,090 | 12/1962 | Taylor . | |
| 3,135,256 | 6/1964 | Gruber | 602/18 |
| 3,164,151 | 1/1965 | Nicoll | 602/18 |
| 3,504,667 | 4/1970 | McFarlane | 602/18 |
| 3,530,853 | 9/1970 | Bond . | |
| 3,756,226 | 9/1973 | Calabrese et al. . | |
| 4,325,363 | 4/1982 | Berkeley | 602/18 |
| 4,401,111 | 8/1983 | Blackstone | 602/18 |
| 4,502,471 | 3/1985 | Owens . | |
| 4,573,456 | 3/1986 | Spann | 602/6 X |
| 4,712,540 | 12/1987 | Tucker et al. | 602/18 |
| 4,987,891 | 1/1991 | Gaylord, Jr. et al. | 602/18 |
| 5,058,575 | 10/1991 | Anderson | 602/18 |
| 5,060,637 | 10/1991 | Schmid et al. | 602/18 |

OTHER PUBLICATIONS

Mikros Product brochure-1988.

Primary Examiner—Stephen R. Crow
Assistant Examiner—Linda C. M. Dvorak
Attorney, Agent, or Firm—Burd, Bartz & Gutenkauf

[57] ABSTRACT

A cervical collar for circumferential placement around the neck of a wearer in order to form a relatively rigid structure around the neck that is capable of bending circumferentially around the neck for a close fit thereon. A soft base is in confronting relationship to the neck. A splint assembly is fixed to the outer surface of the base and includes a plurality of parallel spaced apart upright splints that are uniformly distributed around the neck when the collar is installed thereon. The splints are separated by an expanse of material which forms a hinge. The hinge permits bending of the collar around the neck while holding the splints in place. Ventilation openings can be located in the spacing between adjacent splints in order to provide ventilation to the neck, facilitate bending of the collar about the neck, and to lessen the weight thereof.

10 Claims, 4 Drawing Sheets

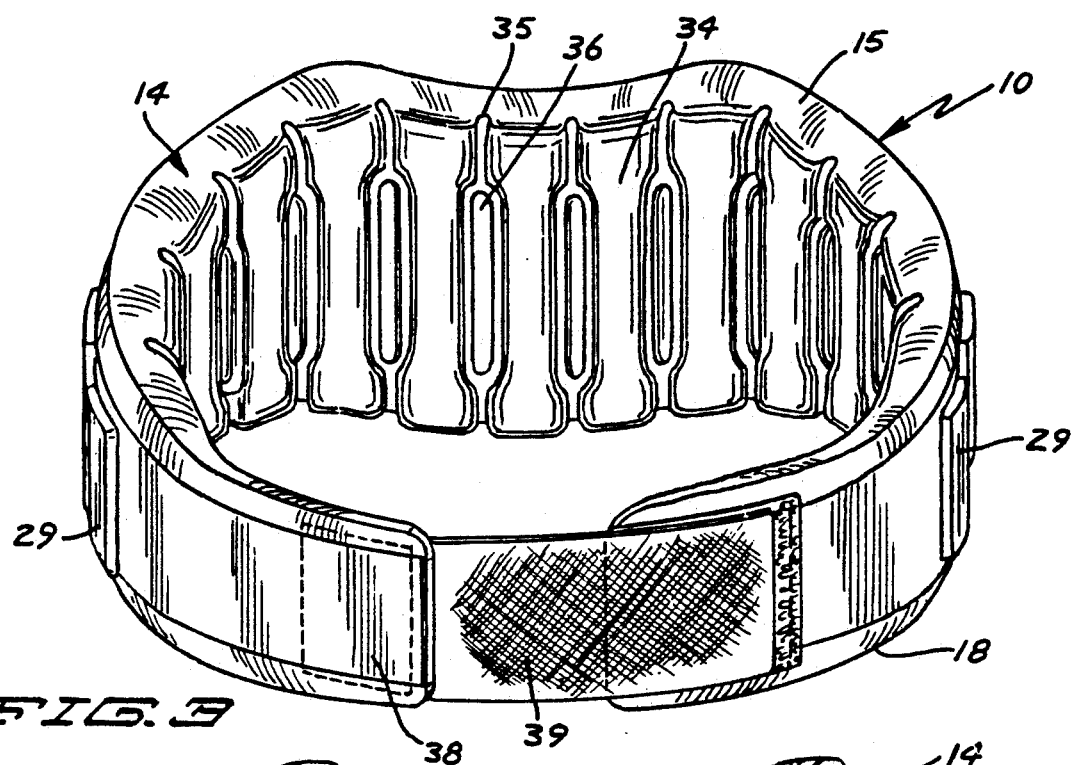
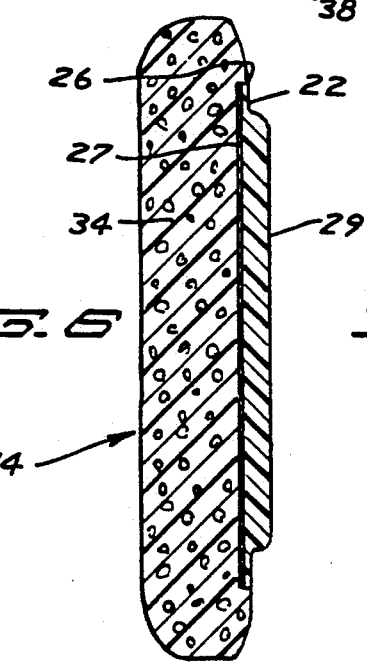
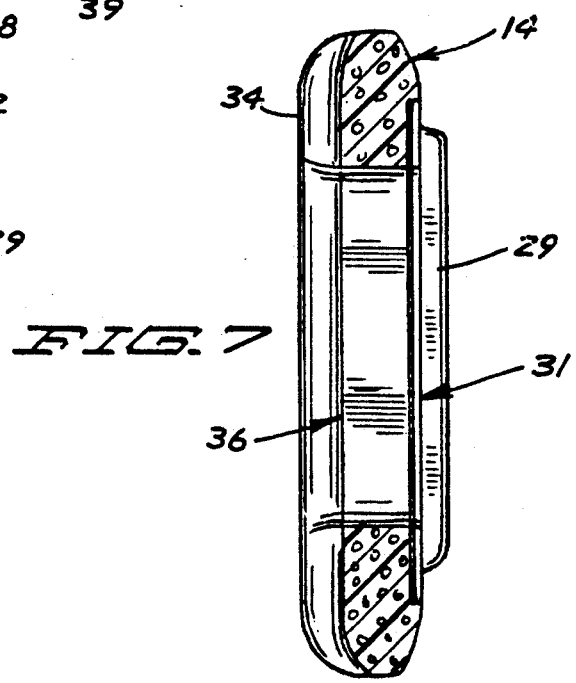
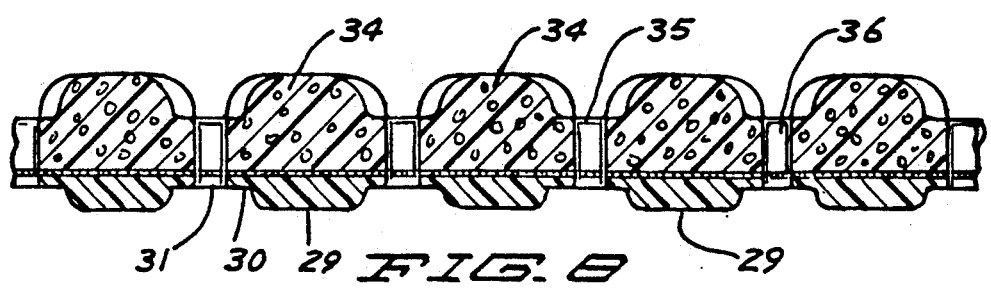

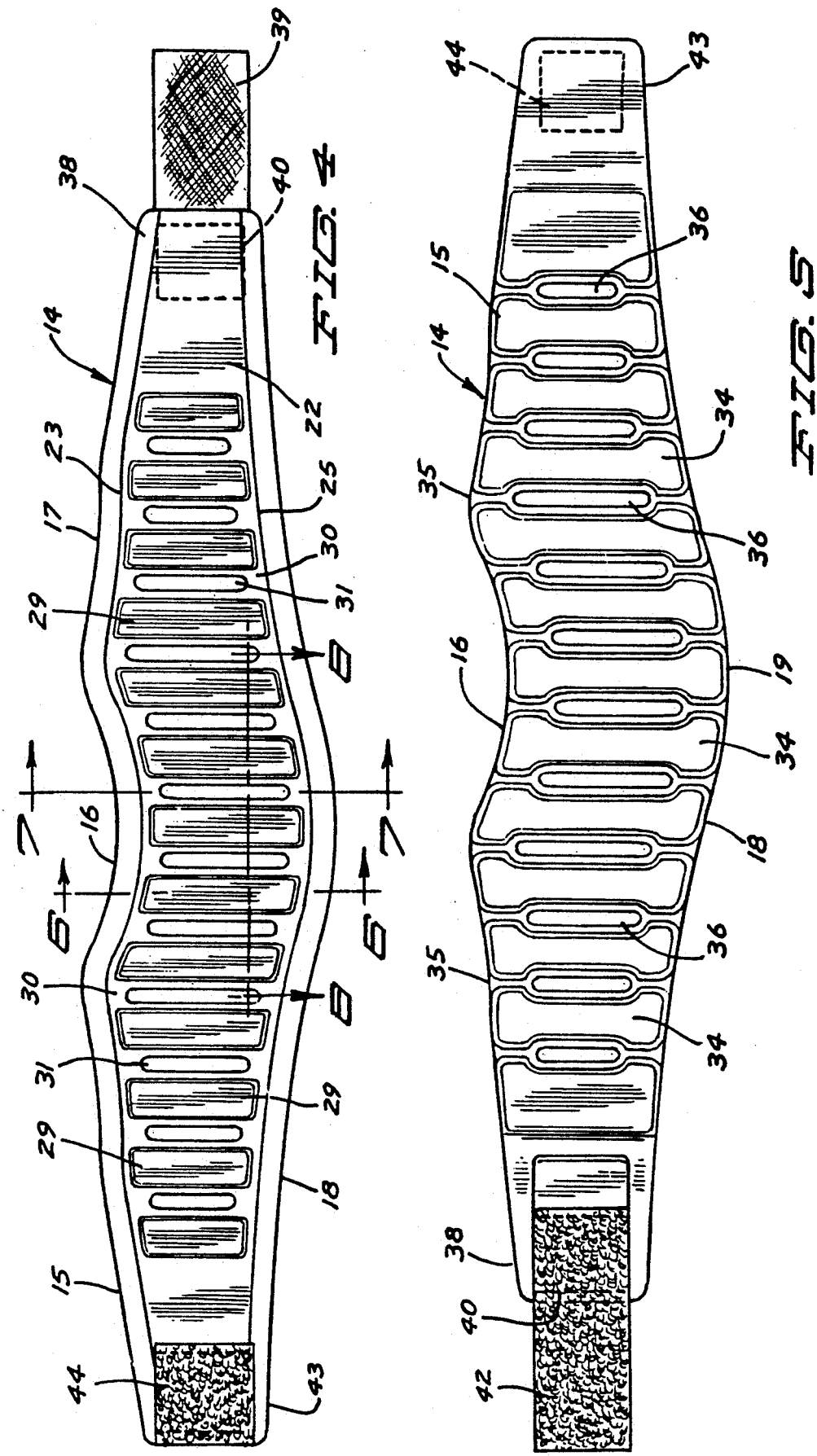

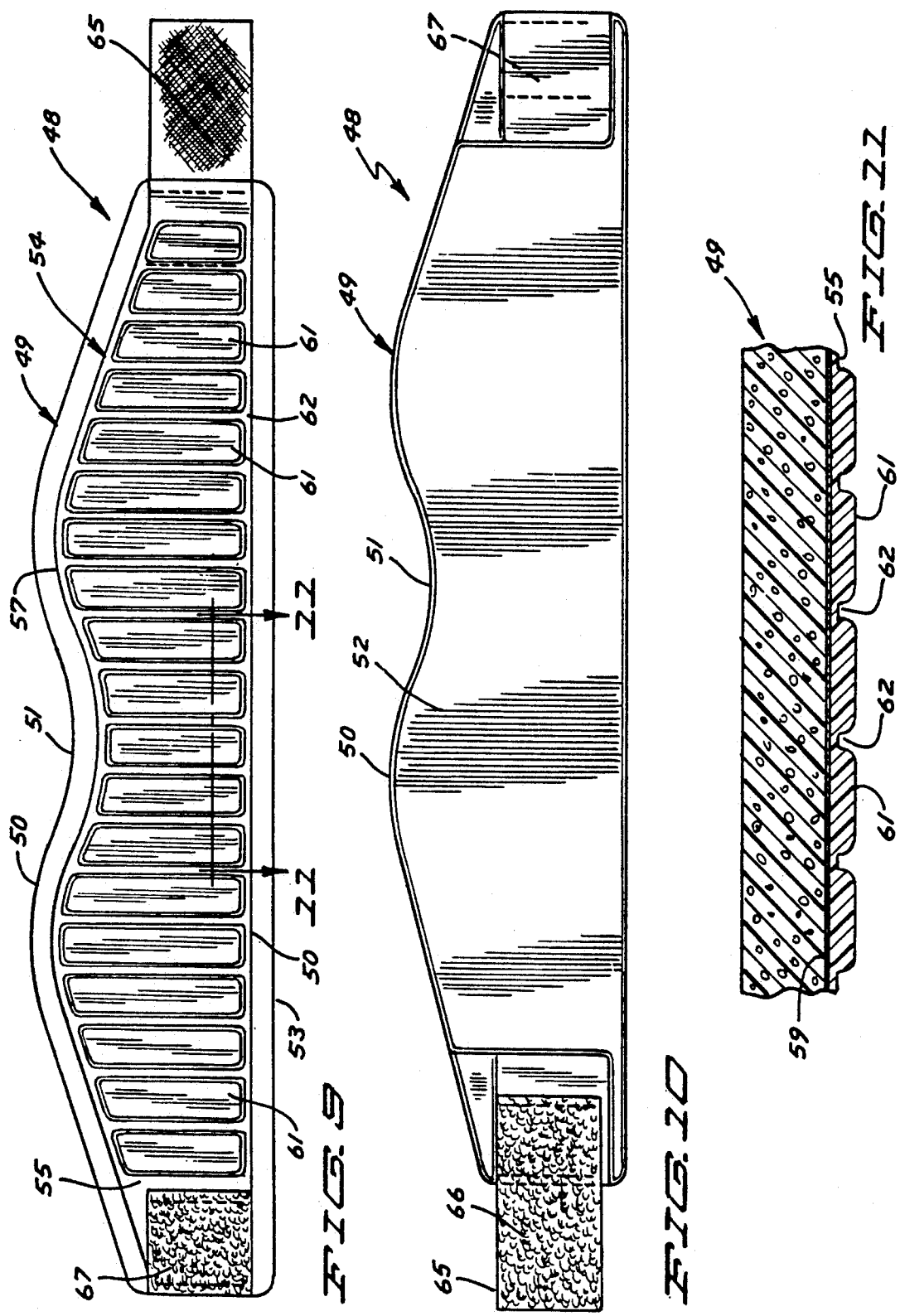

CERVICAL COLLAR

BACKGROUND OF THE INVENTION

The vertebral column of the human skeletal frame, often called the spinal column, is formed of a series of bones called vertebrae. It is a flexible column. The head is balanced on top of the column. The skeletal framework of the neck consists of seven cervical vertebrae. In the cervical region of the spinal column, extension, abduction and rotation (twisting) are more extensive than in any other region. The neck has interior, lateral and posterior groups of muscles to provide and control the versatile movement permitted by the cervical vertebrae. Because of the free mobility of the cervical vertebrae compared with that of the thoracic and lumbar areas, severe neck injuries, while relatively uncommon, require therapeutic treatment that includes immobilization of the cervical region. The neck has been known to be broken (fractured) and dislocated, especially in football and diving. Any severe force that either hyperextends, compresses or twists the neck can cause cervical fracture. Cervical dislocations most often occur at the fourth, fifth or sixth vertebrae. Less severe, but nonetheless significant, injury, occurs upon hyperextension of muscles of the interior, lateral and posterior groups. Upon occurrence of such injuries, the neck requires at least some degree of immobilization in order to heal. Two forms of neck braces or cervical collars are popular. The first provides a pair of relatively rigid halves that come together about the neck and are fastened in some fashion to immobilize the neck. The other involves simply a cervical collar of a soft material such as a low density foam that gives minimal support.

SUMMARY OF THE INVENTION

The invention relates to a neck brace or cervical collar for substantially immobilizing the neck region. The collar has a soft base proportioned and contoured to fit around the neck. The base can be a low density foam so as to fit comfortably on the neck. A splint assembly is fastened to the outer surface of the base or the surface facing away from the neck. The splint assembly includes a plurality of splints that are orientated parallel to the neck when the collar is fitted on the neck. Each splint is relatively rigid and can be formed of a high density foam. The splints are arranged on the base in a parallel spaced apart relationship so as to circumferentially envelope the neck. The space between the splints permits uniform bending of the collar about the neck. The base positions the splints in proper relationship around the neck. The splints immobilize the neck region. In a preferred embodiment, ventilation openings are positioned in the spacing between the splints.

IN THE DRAWINGS

FIG. 3 is a back elevational view in perspective of the cervical collar of FIG. 2;

FIG. 4 is a front elevational view of the cervical collar of FIG. 2 in a spread out or open configuration;

FIG. 5 is a rear elevational view of the cervical collar of FIG. 4;

FIG. 6 is an enlarged sectional view through a portion of the cervical collar of FIG. 4 taken along the line 6—6 thereof;

FIG. 7 is an enlarged sectional view of another portion of the cervical collar of FIG. 4 taken along the line 7—7 thereof;

FIG. 8 is yet a further enlarged sectional view of a portion of the cervical collar of FIG. 4 taken along the line 8—8 thereof;

FIG. 9 is a front elevational view of an alternative embodiment of a cervical collar according to the invention as shown in a spread out or open configuration;

FIG. 10 is a rear elevational view of the cervical collar of FIG. 9; and

FIG. 11 is an enlarged sectional view of a portion of the cervical collar of FIG. 9 taken along the line 11—11 thereof.

DESCRIPTION OF PREFERRED EMBODIMENTS

Figure 1:
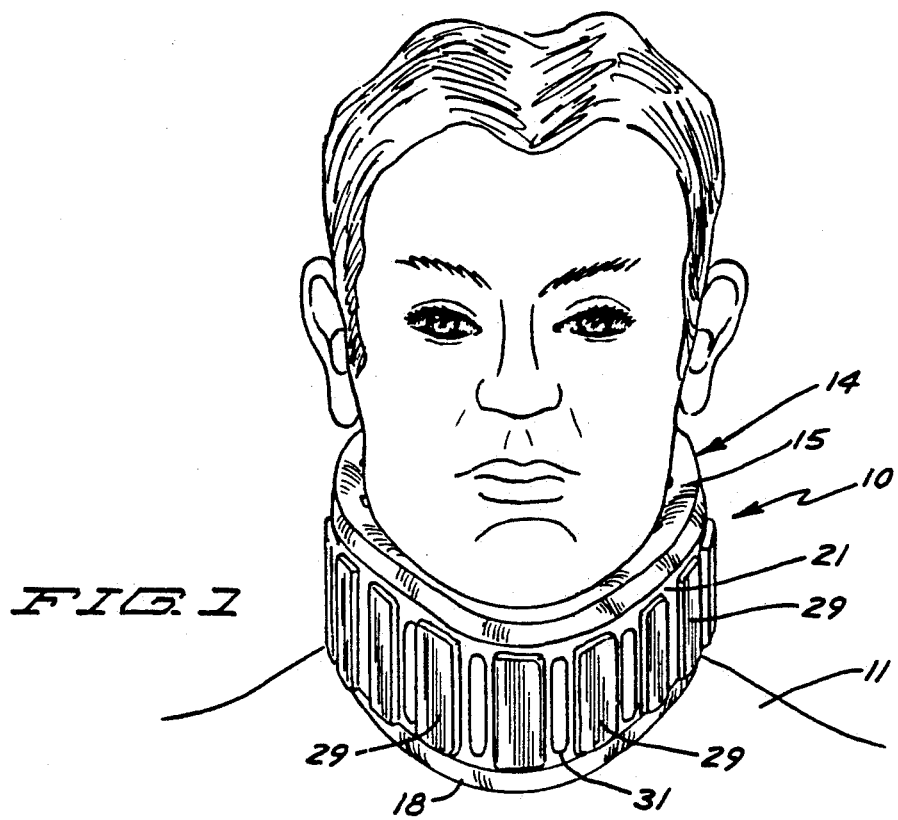
FIG. 1 is a front elevational view of a person wearing a cervical collar according to the invention.

Referring to the drawings, there is shown in FIG. 1, a cervical collar indicated generally at 10 according to the invention and installed on the neck of an individual 11 having a need for cervical immobilization due to injury or disease. Collar 10 substantially immobilizes the cervical vertebrae to restrain movement otherwise caused or provided by the interior, lateral or posterior neck muscles. Immobilization may be required due to damage to the cervical vertebrae or to these muscles themselves. Cervical collar 10 has a soft interior confronting surface which engages the neck for comfort of the individual 11, yet provides firm splint-like resistance to the neck to impede movement thereof.

Cervical collar 10 includes a narrow elongate base 14 proportioned and contoured to extend circumferientially around the neck having an inner surface in confronting engagement with the neck. Base 14 is contoured to fit comfortably about the cervical region of person 11 having an upper edge 15 with a central concave portion 16 for accommodation of the chin of person 11. The ends of base 14 are tapered and of a size to accommodate the restricted neck portion occasioned by the jaw bone. Intermediate dips 17 accommodate the lower jaw. The lower edge 18 of base 14 has a convex region 19 disposed opposite the concave portion 16 for covering the thoracic area of person 11. Base 14 is comprised of a soft, cushion-like material such as a low density foam.

A splint assembly is fastened to base 14 to impart rigidity to collar 10 but permit circumferential bending of collar 10 for conformance to the neck. Splint assembly 21 is fastened to the outer surface of base 14. Splint assembly 21 includes an elongate bendable sheet member 22 embedded on the front surface of base 14 having an upper edge 23 and a lower edge 24 parallel respectively to and spaced inward from the upper and lower edges 15, 18 of base 14. As shown in FIG. 6, the sheet member 22 is accommodated in an indentation 26 formed in the outer surface of the base 14 corresponding to the shape of the sheet member 22. Sheet member 22 can be secured to the base 14 by a glue line 27.

Sheet member 22 carries a plurality of upright, relatively rigid splints 29. Splints 29 are comprised as parallel spaced apart elongate members that ar upright when collar 10 is installed on a neck, or orientated with longitudinal axes generally parallel to the longitudinal axes of the neck. Each splint 29 has a height corresponding to the distance between the upper and lower edges 23, 25 of sheet member 22, and a width narrower than the height. As spacing between the upper and lower edges of the sheet member 22 varies, so necessarily do the heights of the splints 29.

Figure 2:
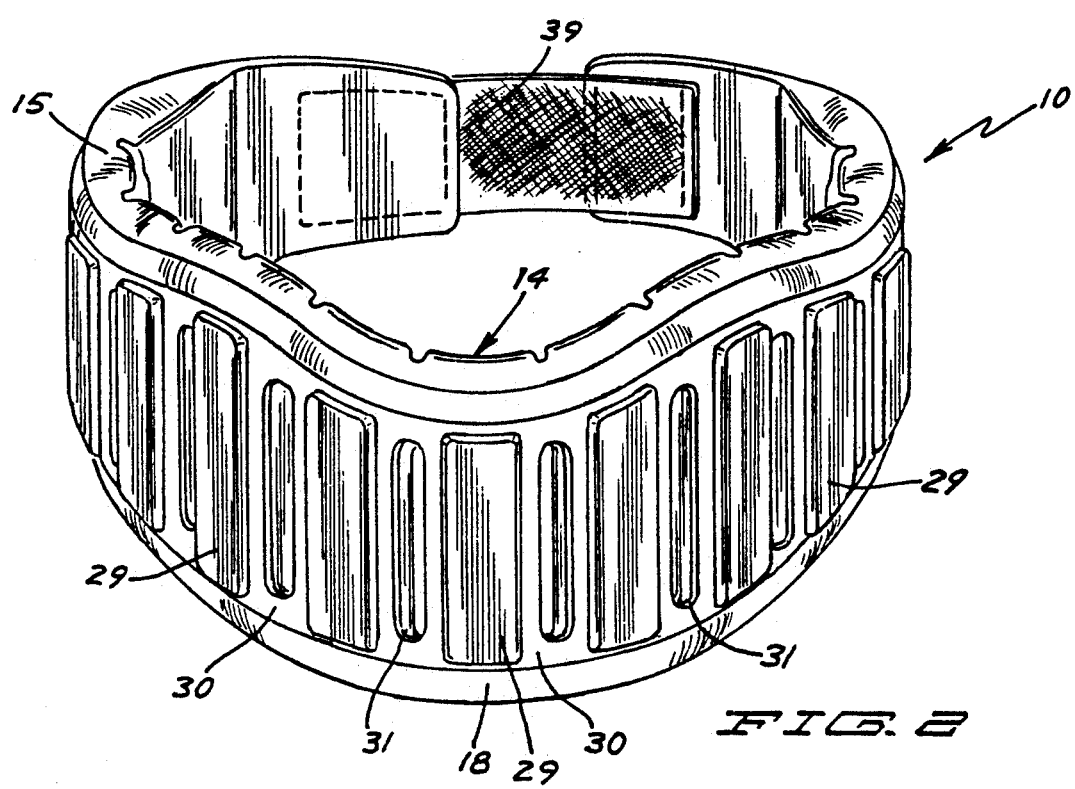
FIG. 2 is an enlarged perspective view of the cervical collar of FIG. 1 in assembled relationship but removed from the person.

Splints 29 are disposed in parallel, uniformly spaced apart relationship along the length of sheet member 22 so as to be uniformly distributed circumferentially around the neck of person 11 when collar 10 is installed thereon. Adjacent splints 29 are circumferentially separated by a short bendable expanse 30 of sheet member 22 forming a live hinge and permitting relative bending between adjacent splints 29 as shown in FIGS. 2 and 3. Hinge sections 30 permit not only outward circumferential bending, but inward bending as well where needed to conform to the neck contour. Thirteen splints separated by twelve openings are shown, although more or less could be provided.

As shown in FIGS. 2 and 4, hinge sections 30 have elongate openings 31 parallel to splints 29 and located between the splints 29. Openings 31 are long and narrow with a major axis parallel to splints 29 and correspond in height almost to that of the splints 29. Openings 31 serve a number of purposes. They allow ventilation to the cervical area. They enhance the bending characteristics of the live hinges 30 between adjacent splints 29, and accordingly of the collar 10. They lessen the weight of the collar.

As shown in FIG. 8, splint assembly 21 can be fashioned as a single piece of material such as a relatively rigid molded foam forming sheet member 22 and the splints 29. By virtue of its small width, sheet member 22 is flexible. Splints 29 are somewhat thicker in width and breadth and therefore acquire a rigid characteristic.

The interior surface of base 14 that confronts the neck is shown in FIGS. 3 and 5. The interior surface of base 14 has a plurality of parallel spaced apart ribs 34. Each rib 34 corresponds to and is located opposite one of the splints 29 on splint assembly 21. Ribs 34 extend the height of base 14 between the upper and lower edges 15, 18 and are connected by upper and lower hinge sections 35 that are relatively narrow compared to the ribs 34 and permit easy bending. Openings 36 are located in base 14 between the ribs 34. The openings 36 are long and narrow and one opening 36 corresponds to and is opened to one of the openings 34 of the sheet member 22. Ribs 34 are of the same soft foam material as the base 14 and are comfortably situated against the neck of the person 10.

Fastening means are provided for securely fastening collar 10 about the neck. A first end 38 of collar 10 carries a fastening strap 39 fastened to the end by suitable means such as a stitching 40. As shown in FIG. 5, the inwardly facing surface of the outer end of fastening strap 39 carries synthetic material 42 of the type that adheres when pressed together and sold under the trademark Velcro. A second end 43 of the collar 10 carries an outwardly facing fastening pad 44 having the mating portion of the synthetic adhering material.

In the use of cervical collar 10, the collar is placed about the neck with the base 14 inwardly facing and positioned such that the concave contour 16 of base 14 is positioned under the chin. The dips 17 engage the jowl area and the ends 38, 43 are brought together at the rear of the neck and fastened using the fastening strap 42 and fastening pad 44. The ribs 34 on the interior confronting surface of base 14 comfortably engage the neck. The hinge portions 30 on the splint assembly 21 and the hinge sections 35 of the base 14 permit circumferential bending of the collar about the neck in conformance with the various contours thereof. The splints 29 are positioned in parallel spaced apart relationship uniformly about the neck in so as to substantially immobilize the neck. The neck is substantially immobilized with a minimum of discomfort to the person 11. Ventilation openings 31 in the splint assembly 21, and the corresponding openings 36 in the base 14 permit ventilation of the cervical area, facilitate bending of the collar about the neck and lessen the weight thereof.

An alternative version of a cervical collar according to the invention is shown in FIGS. 9–11 indicated generally at 48. Cervical collar 48 includes an elongate base 49 proportioned and contoured to extend circumferentially around the neck and having a flat inner surface 52 in confronting engagement with the neck. Base 49 is contoured to fit comfortably around the cervical region of a person, having an upper edge 50 with a central concave portion 51 for accommodation of a chin of a person. The ends of base 49 are tapered and of a size to accommodate the restrictive neck or jowl portion of a person. The lower edge 53 of base 49 is linear. Base 49 is comprised of a soft, cushion like material such as a low density foam.

A splint assembly 54 is fastened to the outer surface of base 49 or the surface opposite the inner surface 52. Splint assembly 54 includes an elongate bendable sheet member 55 fastened on the front surface of base 49 having an upper edge 57 and a lower edge 58. The upper edge 57 and lower edge 58, respectfully, are parallel to and spaced inwardly from the upper and lower edges 50, 53 of the base 49. As shown in FIG. 11, the sheet member 55 is secured to the front surface of base 49 by a glue line 59.

Sheet member 55 carries a plurality of upright, relatively rigid splints 61. Splints 61 are comprised as parallel, circumferentially spaced apart elongate members that are upright when the collar 48 is installed on a neck. Each splint 61 has a height corresponding to the distance between the upper and lower edges 57, 58 of the sheet member 55, and a width narrower than the height. As spacing between the upper and lower edges of the sheet member varies, so necessarily do the heights of the splints.

Splints 61 are disposed in parallel, uniformly spaced apart relationship along the length of sheet member 55 so as to be uniformly distributed circumferentially around the neck of a person when the collar 48 is installed thereon. Adjacent splints 61 are circumferentially separated by a short expanse or hinge section 62 of sheet member 55 forming a live hinge and permitting relative bending between adjacent splints 61. As shown in FIG. 11, splint assembly 54 can be fashioned as a single piece of material such as a relatively rigid molded foam forming the sheet member 55 and the splints 61 along with the hinge sections 62. By virtue of its relatively small width, the sheet member portion of the composite is flexible, while the splints 61 are somewhat thicker in width and breadth and therefore acquire a rigid property.

A fastening strap 65 has a fixed end fixed to one end of the collar 48 and carries at the free end inwardly facing fastening material of the type that adheres when pressed together as indicated at 66. The other end of the collar 48 carries an outwardly facing fastening pad 67 of adhering material. In use, collar 48 is installed upon a neck with the concave portion 51 accommodating the lower chin and the remainder wrapped around for fastening at the rear of the neck with the fastening strap 65 attached to the fastening pad 67. The splints 61 provide immobilizing support to the neck area, and the hinge section 62 readily permit bending of the splint assembly 54 so as to enable proper positioning of the splints with respect to the neck.

While there have been shown and described certain preferred embodiments of the invention, it is apparent that changes can be made from the embodiments shown without departing from the scope and spirit of the invention.

The embodiments of the invention in which an exclusive property or privilege is claimed are defined as follows:

1. A cervical collar for circumferential placement around the neck of a wearer, comprising:
   an elongate base of soft flexible material contoured to extend circumferentially around the neck and having an inner surface for confronting engagement with the neck, said base having an upper edge and a lower edge and first and second ends;
   releasable fastening means connected to the first and second ends of the base for releasably fastening the base in place around a neck;
   a splint assembly fastened to the outer surface of the base opposite the inner surface, to impart rigidity to the collar, said splint assembly including an elongate bendable sheet member secured to the outer surface of the base having an upper edge and a lower edge parallel respectively to the upper edge and lower edge of the base, said sheet member carrying a plurality of upright, relatively rigid splints, said splints comprised as parallel, substantially equally spaced apart elongate members that are upright when the base is installed on the neck, said sheet member and splints being integrally formed of relatively rigid foam plastic, each splint having a height corresponding generally to the distance between the upper and lower edges of the sheet member, adjacent splints being circumferentially separated by a short expanse of sheet member forming a hinge and permitting relative bending movement between adjacent splints as needed to conform to the neck contour, said splints having a width less than the height and greater than the distance between adjacent splints and being uniformly distributed along the length of the sheet member so as to impart uniform rigidity between the upper and lower edges of the sheet member when the collar is installed on the neck of a person.

2. The cervical collar of claim 1 wherein:
   the upper edge of the base has a concave depression for accommodation of the chin.

3. The cervical collar of claim 2 wherein:
   said fastening means includes a fastening strap fixed at one end of the base and having a free end with inwardly facing adhering material, and a fastening pad on the other end of the base having outwardly facing adhering material.

4. A cervical collar for circumferential placement around the neck of a wearer, comprising:
   an elongate base of soft flexible material contoured to extend circumferentially around the neck and having an inner surface for confronting engagement with the neck, said base having an upper edge and a lower edge and first and second ends;
   releasable fastening means connected to the first and second ends of the base for releasably fastening the base in place around a neck;
   a splint assembly including a plurality of upright, relatively rigid splints secured to the outer surface of the base, and splints secured in parallel, substantially equally spaced apart relationship along the length of the base so as to be uniformly circumferentially distributed around the neck in generally parallel relationship to the neck when the base is placed on a neck, said splints separated by bendable base sections serving as hinge sections to facilitate bending of the base around a neck, each such hinge section having a long and narrow opening parallel to the splints, said opening being of uniform width, said splints having a width less than the height and greater than the width of the openings.

5. The cervical collar of claim 4 including:
   a plurality of ribs formed on the inner surface of the base for confronting relationship with the neck and aligned with corresponding splints on the outer surface of the base.

6. The cervical collar of claim 4 including:
   a sheet member secured to the outer surface of the base, said sheet member carrying said splints, said sheet member having hinge sections between adjacent splints, and an elongate opening in each hinge section in alignment with the elongate opening of the base.

7. A cervical collar for circumferential placement around the neck of a wearer, comprising:
   an elongate base of soft flexible material contoured to extend circumferentially around the neck and having an inner surface for confronting engagement with the neck, said base having an upper edge and a lower edge and first and second ends;
   releasably fastening means connected to the first and second ends of the base for releasably fastening the base in place around a neck;
   a splint assembly fastened to the outer surface of the base opposite the inner surface, to impart rigidity to the collar, said splint assembly including an elongate sheet member secured to the outer surface of the base having an upper edge and a lower edge parallel respectively to the upper edge and lower edge of the base, said sheet member carrying a plurality of upright, relatively rigid, equally spaced apart splints, said splints comprised as parallel elongate members that are uniformly spaced apart along the length of the base so as to be uniformly circumferentially distributed about the neck in generally parallel relationship to the neck when the base is installed upon a neck, each splint having a height corresponding generally to the distance between the upper and lower edges of the sheet member, adjacent splints being circumferentially separated by an expanse of sheet member that is relatively short compared to the height of the splint forming a hinge and permitting relative bending movement between adjacent splints as needed to conform to the neck contour;
   a plurality of elongate openings formed in the sheet member of the splint assembly in the expanse between adjacent splints forming the hinge section, and a corresponding plurality of openings in the base aligned with the openings in the sheet member, said openings being substantially uniform width, said splints having a width less than the height and greater than the width of the openings;

a plurality of ribs formed on the inner surface of the base for confronting relationship with the neck and aligned with and corresponding to the plurality of splints on the sheet member.

8. The cervical collar of claim 7 wherein:
the upper edge of the base has a concave depression for accommodation of the chin.

9. The cervical collar of claim 8 wherein:
the upper edge of the base has a pair of intermediate dips for accommodation for the lower portion of the jaw.

10. The cervical collar of claim 9 wherein:
said fastening means includes a fastening strap fixed at one end of the base and having a free end with inwardly facing adhering material, and a fastening pad on the other end of the base having outwardly facing adhering material.

* * * * *